United States Patent
Groh et al.

(10) Patent No.: US 6,980,626 B2
(45) Date of Patent: Dec. 27, 2005

(54) X-RAY ARRANGEMENT AND OPERATING METHOD FOR COMPENSATING SCATTERED RADIATION

(75) Inventors: Burkhard Groh, Erlangen (DE);
Volker Heer, Gundelsheim (DE);
Mathias Hörnig, Erlangen (DE);
Bernhard Sandkamp, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 150 days.

(21) Appl. No.: 10/621,501

(22) Filed: Jul. 17, 2003

(65) Prior Publication Data

US 2004/0079232 A1 Apr. 29, 2004

(30) Foreign Application Priority Data

Jul. 17, 2002 (DE) .......................................... 102 32 429

(51) Int. Cl.⁷ ............................................ G01N 23/201
(52) U.S. Cl. ..................... 378/87; 378/98.11; 378/98.12
(58) Field of Search .............................. 378/70, 86, 87, 378/98.11, 98.12

(56) References Cited

U.S. PATENT DOCUMENTS

2004/0202280 A1 * 10/2004 Besson ........................ 378/37
2004/0228442 A1 * 11/2004 Sakaguchi et al. ............ 378/87

FOREIGN PATENT DOCUMENTS

| DE | PS 195 05 283 | 4/1998 | | |
| DE | OS 198 42 474 | 3/2000 | | |
| JP | 2000102529 A | * 4/2000 | ............ | A61B/6/02 |

* cited by examiner

*Primary Examiner*—Edward J. Glick
*Assistant Examiner*—Chih-Cheng Glen Kao
(74) *Attorney, Agent, or Firm*—Schiff Hardin LLP

(57) ABSTRACT

Method for an x-ray arrangement for compensation of scattered radiation and x-ray apparatus The invention concerns a method for an x-ray arrangement comprising two x-ray systems (1, 2) for compensation of scattered radiation. In addition, the invention concerns an x-ray apparatus with two x-ray systems (1, 2) which respectively comprise an x-ray source (4, 5) and an x-ray detector (5, 7). An x-ray scattered radiation image based on the x-ray radiation (11) scattered on a subject (P) is acquired for at least one of the two x-ray systems (1, 2), given a definite positioning of the x-ray systems (1, 2) relative to one another. The acquired x-ray scattered radiation image is saved and used for subtraction from an x-ray image acquired with the x-ray system (1, 2) in order to compensate for the influence of the scattered radiation originating from the other x-ray system (1, 2) and to achieve an improved image quality.

6 Claims, 2 Drawing Sheets

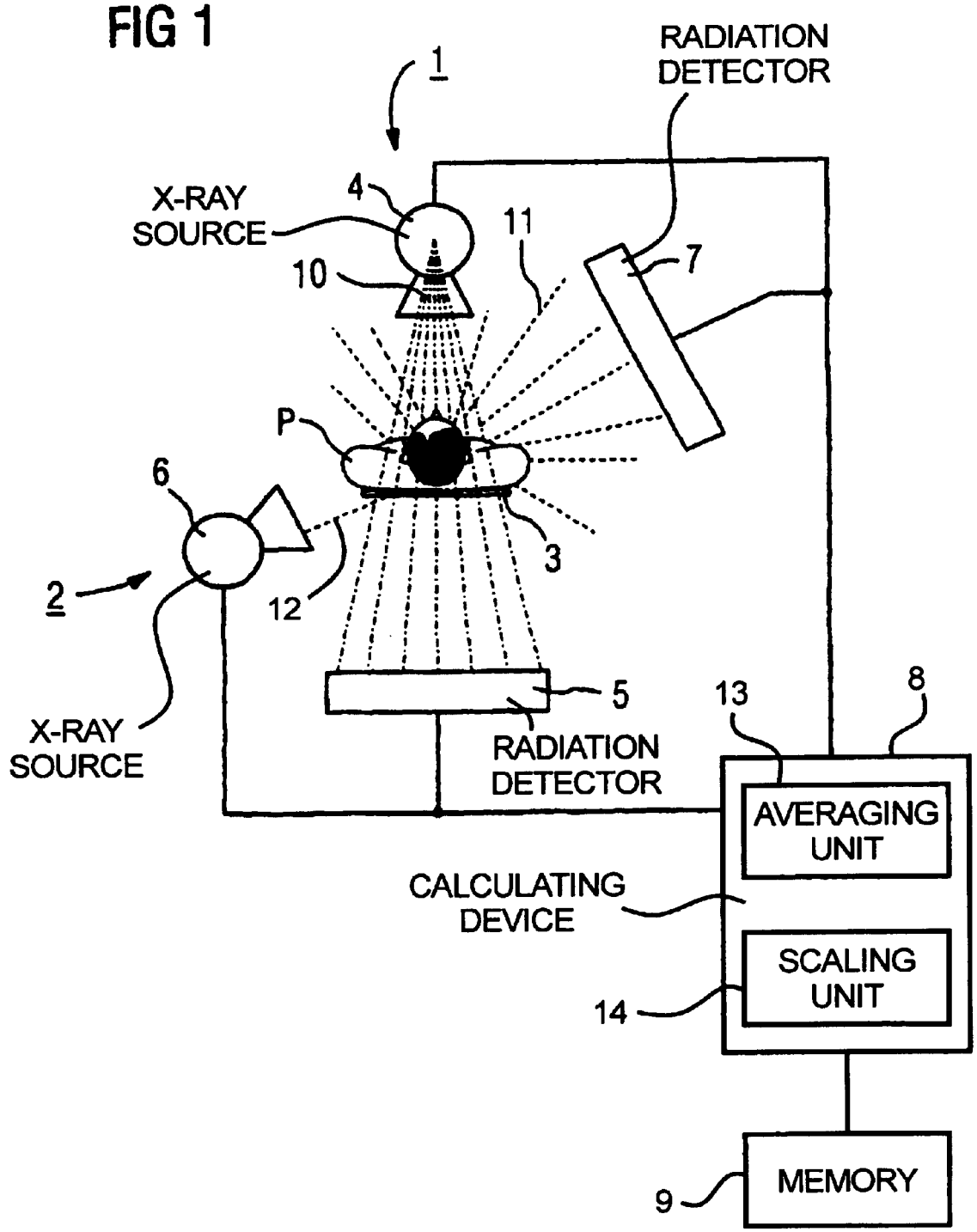

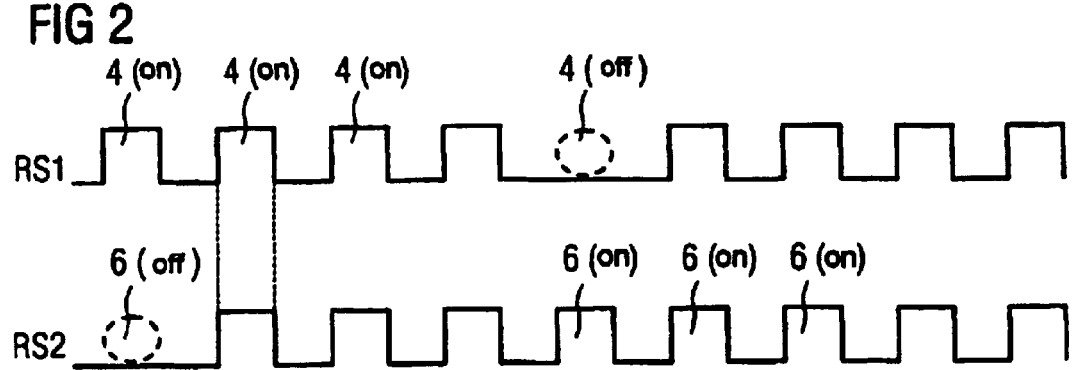
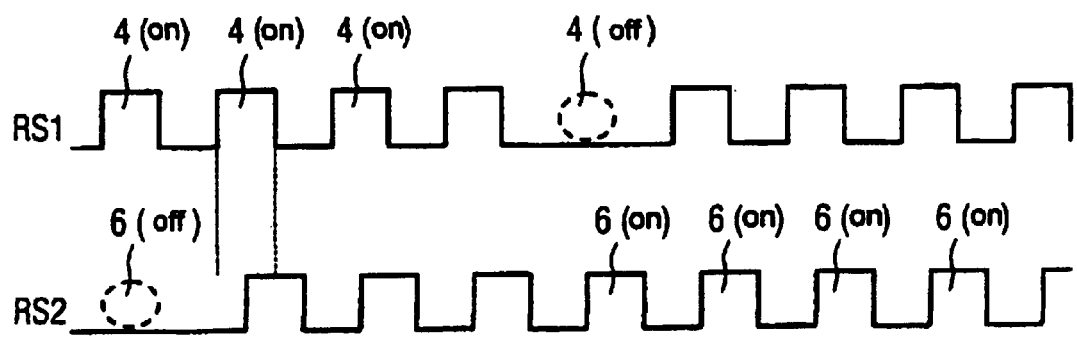

X-RAY ARRANGEMENT AND OPERATING METHOD FOR COMPENSATING SCATTERED RADIATION

The invention concerns a method for an x-ray arrangement for compensation of scattered radiation, which x-ray arrangement comprises two x-ray systems with respectively one x-ray source and one x-ray detector. The invention moreover concerns an x-ray apparatus comprising two x-ray systems.

An x-ray apparatus of the type cited above, for example, is what is known as a biplane x-ray apparatus which is used for cardiological or neurological examinations and treatments of patients. Due to the configuration of the x-ray apparatus with two x-ray systems, it is possible to acquire two x-ray exposures of a body region of a patient practically simultaneously from different angles. This serves primarily to acquire spatial information of this body region.

However, the mutual influence of the two x-ray systems due to the x-ray radiation scattering from the body of the patient thereby turns out to be problematic. This scattered radiation is less-energetic x-ray radiation that is radiated from the body of the patient in all spatial directions upon irradiation of the patient if it is not uniform and doesn't contribute to the usable image information. The scattered radiation has the disadvantageous effect that the image quality of the x-ray image acquired by the x-ray system is degraded. Namely, the scattered radiation also disrupts that x-ray system from whose emitted x-ray radiation the scattered radiation results. However, the largest part of the scattered radiation is again emitted in the direction of the x-ray source of this x-ray system. However, if the x-ray source of the one x-ray system is located near the x-ray detector of the other x-ray system, the interference between the two x-ray systems is particularly large.

In a biplane x-ray arrangement with each employing an x-ray image intensified as the x-ray detector, it is comparatively simple to suppress the scattered radiation, because one x-ray system is always switched "blind", i.e. unreceptive to x-rays, while the other x-ray system is in operation. This has the disadvantage, however, that only temporally displaced x-ray exposures of a patient can be acquired with the two x-ray systems of the biplane x-ray device. A further disadvantage of this technique is that the possibility to switch blind is not present in x-ray detectors of the solid state type, for example aSi detectors. In this case, operation must be undertaken with a reduced image rate in both x-ray systems, which constrains the operator. The effective image rate that would otherwise be available thus is too high to select the useable image rate, which means the systems must be operated below technical capabilities.

Radiation converters in the form of solid state detectors and x-ray image intensifiers are specified in DE 198 42 474 A1 which can be used in biplane x-ray apparatuses. The radiation converters are characterized in that they comprise an luminous layer that emits light upon being impinged by radiation, in particular x-ray radiation, whereby a controllable layer is associated with the luminous layer, which controllable layer is substantially radiation-permeable over its entire surface upon a first activation, and is radiation-impermeable over its entire surface given another activation. Scattered radiation influences or radiation not generated by arranged radiation emitters can be excluded from the signal evaluation in this manner, whereby the image quality can be improved. However, given simultaneous operation of two x-ray systems (for example, in a biplane x-ray apparatus), the influence of the scattered radiation can not be excluded in this manner.

The invention is therefore based on the object to specify a method or, respectively, an x-ray apparatus of the type cited above, such that the influence of the scattered radiation on the image quality is at least reduced.

According to the invention, this object is achieved by a method according to claim 1 as well as by an x-ray apparatus according to claim 4. According to the invention, a subject is preferably irradiated with the x-ray source of the first x-ray system at a specific position of the x-ray systems relative to one another, and a first x-ray scattered radiation image based on the x-ray radiation scattered on the subject is acquired for the second x-ray system with the x-ray detector of the second system, whose x-ray source is not operated during the operation of the x-ray source of the first system. In the same position of the x-ray systems relative to one another, the subject is irradiated with the x-ray source of the second x-ray system and a second x-ray scattered radiation image based on the x-ray radiation scattered on the subject is acquired for the first x-ray system by the x-ray detector of the first x-ray system, whose x-ray source is not operated during the operation of the x-ray source of the second system. The x-ray scattered radiation images acquired thusly are saved in order to subtract the saved second x-ray scattered radiation image from an x-ray image acquired with the first x-ray system or, respectively, to subtract the saved first x-ray scattered radiation image from an x-ray image acquired with the second x-ray system given simultaneous, partially displaced or completely displaced operation of the two x-ray systems, such that the influence of the scattered radiation originating from the second respective x-ray system on the x-ray image acquired by the first respective x-ray system is at least reduced, if not actually eliminated completely. The image quality of x-ray images acquired with the x-ray systems can thus be improved in this manner.

According to a variant of the invention, the x-ray scattered radiation images are acquired and saved under defined acquisition conditions for each x-ray system. The x-ray scattered radiation images are thereby appropriate for the image correction as long as the acquisition conditions remain unchanged in their acquisition as well as in the acquisition of subsequent x-ray images of a subject. The acquisition conditions thereby comprise the x-ray dose, the x-ray spectrum and the acquisition geometry. Since the x-ray scattered radiation images are actually proportional to the x-ray dose, it is possible, given a change of the x-ray dose for the acquisition of further x-ray images, to scale an x-ray scattered radiation image that is consulted for the subtraction corresponding to the change of the x-ray dose. In this manner, given a change of the x-ray dose one is not forced to always acquire and save new x-ray scattered radiation images in order to compensate for the parasitic [sic] scattered radiation in acquired x-ray images of a subject.

A further variant of the invention provides to determine the x-ray scattered radiation image used for an x-ray system for subtraction, such that a plurality of x-ray scattered radiation images which are averaged are acquired for the x-ray system. The averaging over a plurality of x-ray scattered radiation images has the advantage that the statistical noise in the resulting x-ray scattered radiation image is reduced, whereby the image quality is improved. However, the statistical noise of an x-ray scattered radiation image can also be reduced by a low-pass filter, since practically solely low frequency portions are present in x-ray scattered radiation images.

An exemplary embodiment of the invention is shown in the attached schematic drawings. Thereby shown are:

FIG. 1 an x-ray apparatus with two x-ray systems and

FIGS. 2 and 3 operating schematics of the x-ray apparatus shown in FIG. 1.

The x-ray device schematically shown in FIG. 1 has two x-ray systems 1 and 2 that, in the exemplary embodiment, are adjustable around a patient P positioned on a schematically indicated patient positioning device 3. The x-ray system 1 has an x-ray source 4 as well as an x-ray detector 5, and the x-ray system 2 has an x-ray source 6 as well as an x-ray detector 7. The x-ray source 4 and the x-ray detector 5 as well as the x-ray source 6 and the x-ray detector 7 each are preferably arranged on a C-arm (not shown). The x-ray source 4 and the x-ray source 6 respectively emit a conical x-ray beams 10 and 12. In the exemplary embodiment, the x-ray detectors 5 and 7 are solid-state detectors. The x-ray systems 1 and 2 are connected to a calculating device 8. The calculating device 8, which controls the operation of the x-ray device, is additionally connected to memory 9 of the x-ray device.

In the operation of the x-ray device, x-ray exposures of a body region of the patient P can be acquired practically simultaneously from different angles with the two x-ray systems 1 and 2. As explained above, the scattered radiation which is emitted from the body of the patient P in all directions disadvantageously affects the quality of the x-ray recordings of the body region of the patient P acquired with the x-ray systems 1 and 2. The origin of the weaker energy x-ray radiation 11 scattered in the body of the patient P is illustrated in FIG. 1 for the operation of the x-ray system 1, by the x-ray radiation beam 10 being emitted from the x-ray source 4 toward the direction of the patient P, as well as toward the x-ray detector 5. As can be seen in FIG. 1, although the scattered radiation 11 is not uniform, it nevertheless radiates in all directions as well as in the direction of the x-ray detector 7 of the x-ray system 2. The scattered radiation 11 contributes no useful information for the acquisition of x-ray images with the x-ray detector 7. Furthermore, the image quality of the x-ray recordings acquired with the x-ray detector 7 is degraded by the scattered radiation 11. The same is true for scattered radiation which strikes upon the x-ray detector 5 of the x-ray system 1, when an x-ray beam is emitted from the x-ray source 6,of the x-ray system 2 in the direction of the patient P and the x-ray detector 7.

In order to at least reduce the negative influence of the generated scattered radiation on the imaging with the two x-ray systems 1 and 2, it is therefore proposed to irradiate the patient P with the x-ray source 4 of the x-ray system 1 for a definite position of the two x-ray systems 1 and 2 relative to one another and to acquire a first x-ray scattered radiation image based on the radiation scattered on the patient P with the x-ray detector 7, whose x-ray source 6 is not in operation during the irradiation by the x-ray source 4. This first x-ray scattered radiation image is stored by the computer 8 in the storage 9 as correction image for the x-ray detector 7. Given the same position of the x-ray systems 1 and 2 relative to one another, the patient P is irradiated with the x-ray source 7 of the x-ray system 2, and a second x-ray scattered radiation image based on the radiation scattered on the patient P, which is provided for the correction of an x-ray image acquired with the x-ray receiver 5 and stored by a computer 8 in the storage 9, is acquired with the x-ray detector 5 of the x-ray system 1 whose x-ray source 4 is not in operation during the irradiation of the patient P with the x-ray source 6.

Preferably, a number of such x-ray scattered radiation images are acquired for the two x-ray detectors of the x-ray systems 1 and 2, and are averaged in an averaging unit 13, such that a resulting x-ray scattered radiation image is obtained which exhibits reduced statistical noise, for each x-ray system.

If x-ray exposures of a body region of the patient P are thus simultaneously acquired with both x-ray systems 1 and 2 in the operation of the x-ray apparatus, the x-ray images acquired with the x-ray detector 7 can be improved with regards to their quality by subtraction of the first x-ray scattered radiation image saved in the storage 9. Likewise, the x-ray images acquired with the x-ray detector 5 can be improved in quality by subtraction of the second x-ray scattered radiation image saved in the storage 9. The subtraction of an x-ray scattered radiation image from an x-ray image acquired with one of the two x-ray detectors 5 and 7 is implemented by the computer 8. The x-ray images so corrected can finally be displayed in a known manner on a display device (not shown).

Normally, x-ray scattered radiation images for the two x-ray detectors 5 and 7 are determined and stored in the memory 9 for different positions of the x-ray systems 1 and 2 relative to one another in the previously described manner. The determination of the x-ray scattered radiation images thereby ensues according to defined acquisition conditions, such as x-ray spectra, x-ray dosages, and acquisition geometries. If, given the same position of the x-ray systems 1, 2 relative to one another and an unchanged position of the patient P on the patient positioning device 3, only the x-ray dosage changes, then no new x-ray scattered radiation image must be determined. The x-ray scattered radiation images are proportional to the x-ray dosage. If the x-ray sources 4 and 6 emit x-rays at respectively different doses (as schematically indicated in FIG. 1 by the lower number of rays in the beam 12 compared to the beam 10), a scaling of the x-ray scattered radiation images corresponding to the change of the x-ray dosage can ensue in a scaling unit 14, and the respective x-ray scattered radiation images required for the subtraction can be determined in this manner.

Two operation schematics for the operation of the x-ray systems 1 and 2 as well as for the determination of x-ray scattered radiation images are exemplarily illustrated in FIGS. 2 and 3. As can be learned from FIG. 2, the x-ray systems 1 and 2 are operated by the computer 8 such that simultaneous x-ray exposures of a body region of the patient P are acquired. As shown in FIG. 2, the x-ray source 6 is temporarily not operated for the determination of the x-ray scattered radiation image relevant for the x-ray detector 7. The same is true for the x-ray source 4 given the determination of the x-ray scattered radiation image relevant to the x-ray detector 5.

As is shown in FIG. 3, x-ray scattered radiation images also can be determined given temporally shifted operation of the two x-ray systems 1 and 2, since the scattered radiation has influence in this operation as well on the image quality of the x-ray images determined by the two x-ray systems 1 and 2. As a rule, x-ray scattered radiation images for the correction of the x-ray images determined by the two x-ray systems 1 and 2 therefore are also acquired dependent upon the type of operation of the x-ray device, i.e. with regard to the temporal displacement of the acquisition of x-ray images.

The invention was previously described with an example of an x-ray apparatus comprising two x-ray systems. In particular, however, the inventive method can also be executed with an x-ray arrangement with two x-ray apparatuses capable of being operated independently of one another.

What is claimed is:

1. A method for operating an x-ray arrangement to compensate for scattered radiation, said x-ray arrangement comprising a first x-ray system having a first x-ray source and a first x-ray detector and a second x-ray system having a second x-ray source and a second x-ray detector, said method comprising the steps of:

with said first and second x-ray systems in a specified position relative to each other, irradiating a subject with x-rays from said first x-ray source, thereby producing scattered radiation, and detecting said scattered radiation with the second x-ray detector with said second x-ray source being unactivated, thereby obtaining a scattered radiation image from said second x-ray detector;

saving said scattered radiation image;

operating both of said first and second x-ray systems to obtain diagnostic x-ray images of said subject and subtracting said scattered radiation image from the diagnostic images obtained from said second x-ray system; and obtaining said scattered radiation image using a first x-ray dose from said first x-ray source and obtaining said diagnostic images using a second x-ray dose from said second x-ray source, different from said first x-ray dose, and scaling said scattered radiation image, prior to subtraction from said diagnostic images obtained from said second x-ray source, dependent on a relationship between said first x-ray dose and said second x-ray dose.

2. A method as claimed in claim 1 comprising the additional steps of:

with said first and second x-ray systems in said specified position, irradiating said subject with x-rays from said second x-ray source, thereby producing further scattered radiation, and detecting said further scattered radiation with said first x-ray detector and with said first x-ray source being unactivated, thereby obtaining a further scattered radiation image;

saving said further scattered radiation image; and subtracting said further scattered radiation image from said diagnostic images obtained with said first x-ray system.

3. A method as claimed in claim 1 comprising acquiring a plurality of scattered radiation images with said first x-ray source and said second radiation detector, averaging said plurality of scattered radiation images to obtain an average scattered radiation image, and subtracting said average scattered radiation image from said diagnostic images obtained from said second source.

4. An x-ray arrangement comprising:

a first x-ray system having a first x-ray source and a first x-ray detector;

a second x-ray system having a second x-ray source and a second x-ray detector;

a control unit for activating said first x-ray source, with said second x-ray source unactivated, to irradiate a subject with x-rays with said first and second x-ray systems in a specified position relative to each other, thereby producing scattered radiation which is detected by the second x-ray detector, thereby obtaining a scattered radiation image from said second x-ray detector;

a memory in which said scattered radiation image is stored;

said control unit operating both of said first and second x-ray systems to obtain x-ray diagnostic images of said subject and subtracting said scattered radiation image from the diagnostic images obtained from said second x-ray system to compensate for said scattered radiation therein; and said control unit activating said first x-ray source to obtain said scattered radiation image using a first x-ray dose and activates said second x-ray source to obtain said diagnostic images using a second x-ray dose, different from said first x-ray dose, and scales said scattered radiation image, prior to subtraction from said diagnostic images obtained from said second x-ray source, dependent on a relationship between said first x-ray dose and said second x-ray dose.

5. An x-ray arrangement as claimed in claim 4 wherein the control unit, with said first and second x-ray systems in said specified position, activates said second x-ray source, with said first x-ray source unactivated, to irradiate the subject with x-rays, thereby producing further scattered radiation which is detected with said first x-ray detector, thereby obtaining a further scattered radiation image, said further scattered radiation image being stored in said memory, and said control unit subtracting said further scattered radiation image from said diagnostic images obtained with said first x-ray system to compensate said further scattered radiation therein.

6. An x-ray arrangement as claimed in claim 4 wherein said control unit activates said first x-ray source to obtain a plurality of scattered radiation images with said first x-ray source and said second radiation detector, and averages said plurality of scattered radiation images to obtain an average scattered radiation image, and subtracts said average scattered radiation image from said diagnostic images obtained from said second x-ray source.

* * * * *